(12) United States Patent
Karavas et al.

(10) Patent No.: US 8,835,486 B2
(45) Date of Patent: Sep. 16, 2014

(54) PHARMACEUTICAL FORMULATION CONTAINING AN HMG-COA REDUCTASE INHIBITOR AND METHOD FOR THE PREPARATION THEREOF

(76) Inventors: Evangelos Karavas, Pallini-Attikis (GR); Efthimios Koutris, Pallini-Attikis (GR); Elisavet Ioannidou, Pallini-Attikis (GR); Eleni Stathaki, Pallini-Attikis (GR); Dimitrios Bikiaris, Thessaloniki (GR)

( * ) Notice: Subject to any disclaimer, the term of this patent is extended or adjusted under 35 U.S.C. 154(b) by 1321 days.

(21) Appl. No.: 12/063,447

(22) PCT Filed: May 12, 2006

(86) PCT No.: PCT/EP2006/004468
§ 371 (c)(1),
(2), (4) Date: Feb. 11, 2008

(87) PCT Pub. No.: WO2007/131517
PCT Pub. Date: Nov. 22, 2007

(65) Prior Publication Data
US 2010/0137400 A1     Jun. 3, 2010

(51) Int. Cl.
*A61K 31/40*     (2006.01)
*A61K 31/405*    (2006.01)
*A61K 31/727*    (2006.01)
*A61K 9/20*      (2006.01)

(52) U.S. Cl.
CPC ............... *A61K 9/205* (2013.01); *A61K 31/40* (2013.01)
USPC ............................. 514/419; 514/55; 514/415

(58) Field of Classification Search
USPC .................................... 514/415, 419
See application file for complete search history.

(56) References Cited

U.S. PATENT DOCUMENTS

2008/0033030 A1*    2/2008   Capua et al. ................. 514/419

FOREIGN PATENT DOCUMENTS

WO    WO2005/074915 A1 *   8/2005

OTHER PUBLICATIONS

Gupta et al. (European Journal of Pharmaceutics and Biopharmaceutics, vol. 51, pp. 241-248; 2001).*

* cited by examiner

*Primary Examiner* — Paul Zarek
*Assistant Examiner* — George W Kosturko
(74) *Attorney, Agent, or Firm* — AKC Patents LLC; Aliki K. Collins

(57) ABSTRACT

An improved pharmaceutical formulation for oral administration includes a therapeutically effective quantity of an active ingredient and a stabilizer. The active ingredient is Fluvastatin, or pharmaceutically acceptable salts thereof, and the stabilizer is a mixture of Carrageenans. The stabilizer inhibits isomerization, and/or elimination, and/or oxidation and/or recrystallization of the active ingredient.

9 Claims, 4 Drawing Sheets

PHARMACEUTICAL FORMULATION CONTAINING AN HMG-COA REDUCTASE INHIBITOR AND METHOD FOR THE PREPARATION THEREOF

TECHNICAL FIELD OF THE INVENTION

The present invention relates to improved pharmaceutical formulation for oral administration comprising a therapeutically effective quantity of an HMG-CoA reductase inhibitor, and more particularly Fluvastatin, Atorvastatin or salts thereof in combination with a linear sulphated polysaccharide such as Carrageenan and a method for the preparation thereof.

BACKGROUND OF THE INVENTION

Hypercholesterolemia is related to an increased risk of heart diseases. A very effective way to reduce serum cholesterol levels is to inhibit the enzyme 3-hydroxy-3-methylglutaryl coenzyme A (HMG-CoA) reductase, which is a main enzyme in the regulation of cholesterol biosynthesis. The HMG-CoA reductase inhibitors, commonly known as "statins", act through the inhibition of 3-hydroxy-3-methylglutaryl-coenzyme A (HMG-CoA) reductase. This enzyme catalyzes the conversion of HMG-CoA to mevalonate, an early and rate-limiting step in cholesterol biosynthesis. Statins are useful in the treatment of hypercholesterolemia and associated diseases but are extremely susceptible to degradation at pH below 8. Statins at pH below 8 and particularly in acidic conditions, undergo elimination or isomerization or oxidation reactions to form conjugated unsaturated aromatic compounds, as well as the threo isomer, the corresponding lactones and other degradation products. Statins are particularly sensitive to an acidic environment (a low pH environment), in which hydroxyl acids are degraded into lactone. The tendency of HMG-CoA reductase inhibitors to degrade may be accelerated by possible interactions with other active ingredients or excipients present in the composition.

Fluvastatin sodium, is the [R*,S*-(E)]-(±)-7-[3-(4-fluorophenyl)-1-(1-methylethyl)-1H-indol-2-yl]-3,5-dihydroxy-6-heptenoic acid, monosodium salt and Atorvastatin calcium, is the [R—(R*,R*)]-2-(4-fluorophenyl)-b,d-dihydroxy-5-(1-methylethyl)-3-phenyl-4[(phenylamino)carbonyl]-1H-pyrrole-1-heptanoic acid, calcium salt (2:1) trihydrate. Fluvastatin and Atorvastatin are two statins particularly useful in therapeutics but prone to degradation reactions. The degradation of the active ingredient results in reduced effectiveness and treatment failure.

Furthermore, the stability of pharmaceutical compositions containing a HMG-CoA reductase inhibitor and in particular, Fluvastatin or Atorvastatin or salts thereof can also be influenced by the selection of the excipients.

Moreover, the poor flow properties of certain Statins may also generate difficulties when it has to be formulated in dosage forms suitable for oral administration, such as tablets, capsules, caplets, sachets or other solid dosage forms, thus limiting the choices of the excipients that can really be used.

Various methods are already known for the industrial preparation of oral dosage forms comprising a HMG-CoA reductase inhibitor e.g. Fluvstatin or Atorvastatin or salts thereof, as an active ingredient due to its useful therapeutical properties. However, the prior art has encountered substantial difficulties in the production of the oral solid formulations of a desirable stability due to the degradation of said active ingredient.

EP 0 547 000 discloses a stabilized pharmaceutical composition which comprises a statin and an alkaline stabilizing medium capable of imparting a pH of at least 8 to an aqueous solution or dispersion of the composition.

EP 1 148 872 discloses a stable solid pharmaceutical formulation comprising a statin and a buffering agent, such as a carbonate buffer or phosphate buffer, capable of adjusting the pH of the total formulation in the range from 6 to 9.

Furthermore, in EP 1 292 293 is disclosed a composition comprising a homogenous mixture of a statin with a buffering or basifying substance obtained by co-crystallization and/or co-precipitation of the statin and the buffering or basifying substance.

In addition, in long-lasting treatments such as hypercholesterolemia it is very important that the plasma concentration of the drug is constant. For this purpose, in order to attain and maintain constant levels of active ingredient in the plasma retard compositions are used from which the active ingredient is released into the biological system during several hours, typically more than 3 hours and less than 30 hours.

Several different types of formulations exist to obtain sustained release of a drug. In general sustained release can be obtained according to the following mechanisms:

i) Formulation of the drug in a swellable insoluble matrix. In this case, the gastrointestinal fluid penetrates the matrix, which swells, and the drug is dissolved and diffuses through the swelled matrix. The solubility and the dissolution rate of the drug, the swelling kinetics and the pores of the matrix are the key factors affecting the overall release rate.

ii) Formulation of the drug in an eroding matrix basically consisting of soluble polymer. The drug release is controlled by the erosion rate and the swelling rate of the matrix. This system is not indicated for a highly soluble drug.

iii) Diffusion control membrane systems. The membrane is consisted of insoluble but porous polymers and surrounds usually particles or cores containing the drug. Water penetrates the membrane, dissolves the drug, which comes out through the membrane pores. The number and size of the pores as well as the solubility of the drug are the most important factors for the overall release.

iv) Osmotic system. A semi-permeable membrane with one or more orifice surrounds a core. The size of the orifice controls the release of the drug which is achieved via the osmosis phenomenon. This system requires special equipment and is considered expensive.

Fluvastatin's solubility in water (>50 g/l) does not allow the use of eroding matrix systems for a sustained release formulation, while an osmotic system would not be the preferred approach mainly for cost reasons. In swellable insoluble matrices the polymer hydrates and swells to form around the tablet a gellified layer that represents a diffusion barrier for the release of the drug. In this case and especially for highly soluble drugs an initial high drug release rate occurs (initial burst). Furthermore the release rate usually decreases depending on the square of time ($\sim t^2$).

Diffusion control systems, on the other hand, suffer from the well-known burst effect during the initial stage of drug release. Furthermore, they do not provide zero order release profile, which is the optimal for sustained release systems. Moreover, diffusion control systems require complicated manufacturing processes due to the additional steps for the coating application. Fluvastatin is a highly soluble drug so these phenomena occur at greater extend when the formulation is a classical matrix or diffusion control system.

EP 0 948 320 discloses a sustained release pharmaceutical composition comprising a water soluble salt of fluvastatin in a matrix formulation or diffusion-controlled membrane coated formulation.

Although each of the above patents represents an attempt to overcome the instability problems associated with pharmaceuticals compositions for immediate or sustained release comprising a HMG-CoA reductase inhibitor, there still exists a need for improving the stability and release rate of such pharmaceutical compositions without producing unwanted pharmaceutical effects and with low production costs.

SUMMARY OF THE INVENTION

It is, therefore, an object of the present invention to provide an improved solid dosage formulation containing a HMG-CoA reductase inhibitor, and in particular Fluvastatin or Atorvastatin or pharmaceutical acceptable salts thereof as an active ingredient, which overcomes the deficiencies of the prior art and avoids the degradation of the active substance.

It is another object of the present invention to provide a solid pharmaceutical dosage formulation containing a HMG-CoA reductase inhibitor, and in particular Fluvastatin or Atorvastatin or pharmaceutical acceptable salts thereof as an active ingredient having an increased chemical stability of the active ingredient.

Moreover, it is another object of the present invention to provide a stable solid dosage formulation containing a HMG-CoA reductase inhibitor, and in particular Fluvastatin or Atorvastatin or pharmaceutical acceptable salts thereof as an active ingredient, for sustained release providing zero order dissolution profile and with no initial burst effect.

A further aspect of the present invention is to provide a method for the preparation of a stable solid dosage formulation containing a HMG-CoA reductase inhibitor, and in particular Fluvastatin or Atorvastatin or pharmaceutical acceptable salts thereof as an active ingredient, thereby stabilizing said active ingredient and improving the flow properties and the pharmacotechnical characteristics of the formulation.

Still, another aspect of the present invention is to provide a method for the preparation of a stable solid dosage formulation containing a HMG-CoA reductase inhibitor, and in particular Fluvastatin or Atorvastatin or pharmaceutical acceptable salts thereof as an active ingredient adapted for sustained release providing zero order profile and with no initial burst effect.

In accordance with the above objects of the present invention, a pharmaceutical composition is provided comprising an HMG-CoA inhibitor or a pharmaceutical acceptable salt thereof as an active ingredient, and an effective amount of a linear sulphated polysaccharide or mixtures thereof such as Carrageenan as a stabilizer, to inhibit isomerization and/or elimination and/or oxidation and/or re-crystallization.

According to another embodiment of the present invention, a process for the preparation of a solid dosage form for oral administration such as a tablet, capsule or sachet containing a HMG-CoA reductase inhibitor or a pharmaceutical acceptable salt thereof as an active ingredient and an effective amount of a linear sulphated polysaccharide or mixtures thereof such as Carrageenan as a stabilizer to inhibit isomerization and/or elimination and/or oxidation and/or re-crystallization, is provided which comprises:

Forming a homogenous mixture by mixing the total quantity of said active ingredient with the total quantity of said linear sulphated polysaccharide or mixtures thereof;

Kneading the above mixture with a suitable water-free solvent such as absolute ethanol, acetone or mixtures thereof;

Drying the wetted mass;

Sieving the dried mass and adding to the sieved mixture the total quantities of at least one optional excipient such as a binder, a diluent, a disintegrant, a lubricant and/or a glidant and mixing until uniform, and Formulating the resulting mixture in a solid dosage form either by compressing it into a desired tablet form or by filling capsules or sachets.

Further, according to another embodiment of the present invention, a process for the preparation of solid dosage form such as a tablet, a capsule and a sachet, containing a HMG-CoA reductase inhibitor, and in particular Fluvastatin or Atorvastatin or pharmaceutical acceptable salts thereof as an active ingredient and an effective amount of a linear sulphated polysaccharide or mixtures thereof, such as Carrageenan as a stabilizer to inhibit isomerization and/or elimination and/or oxidation and/or re-crystallization is provided, which comprises:

Forming a homogenous mixture by mixing the total quantity of said active ingredient with the total quantity of said linear sulphated polysaccharide or mixtures thereof;

Sieving the above mixture through a sieve;

Adding to the sieved mixture the total quantities of at least one optionally excipient such as a binder, a diluent, a disintegrant, a lubricant and/or a glidant and mixing until uniform, and Formulating the resulting mixture in a solid dosage form by compressing it into a desired tablet form with a force more than 400 kp.

Further preferred embodiments of the present invention are defined in dependent claims 2 to 14 and 17 to 20.

Other objects and advantages of the present invention will become apparent to those skilled in the art in view of the following detailed description.

DETAILED DESCRIPTION OF THE INVENTION

Figure 1:
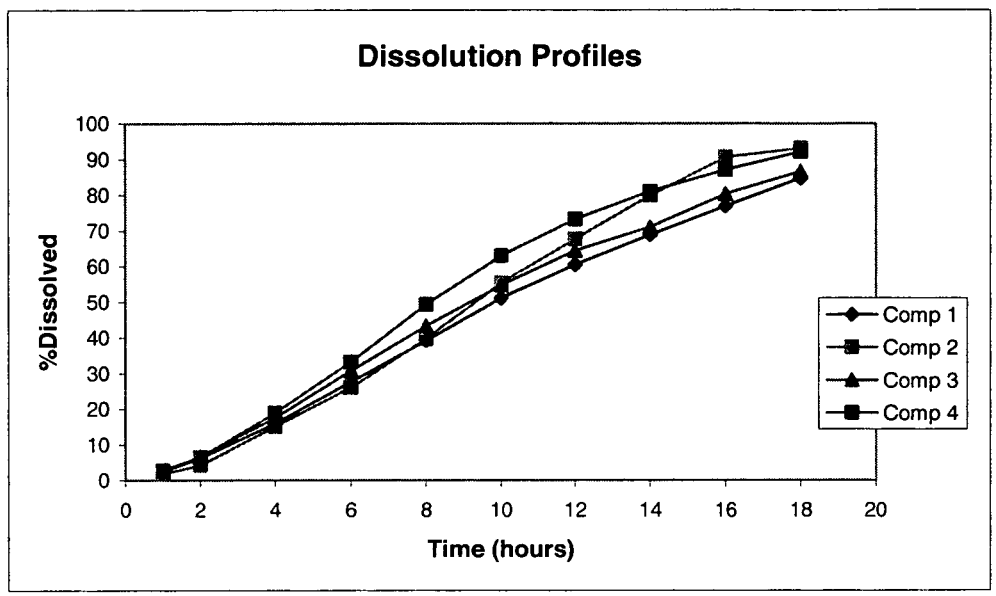
FIG. 1 shows dissolution profiles of 80 mg tablets according to the present invention.

For the purposes of the present invention, a pharmaceutical composition comprising an active ingredient (HMG-CoA reductase inhibitor e.g. Fluvastatin or Atorvastatin or salts thereof) is considered to be "stable" if said ingredient degradates less or more slowly than it does on its own and/or in known pharmaceutical compositions.

An excipient is considered to be "incompatible" with an active ingredient (HMG-CoA reductase inhibitor e.g. Fluvastatin or Atorvastatin or salts thereof) if it promotes the degradation of said active ingredient, that is to say, if said active ingredient (HMG-CoA reductase inhibitor e.g. Fluvastatin or Atorvastatin or salts thereof) degrades more or faster in the presence of said excipient when compared with the degradation of said active ingredient (HMG-CoA reductase inhibitor e.g. Fluvastatin or Atorvastatin or salts thereof) on its own. The terms "incompatibility", "compatible" and "compatibility" are defined accordingly.

The active ingredient (HMG-CoA reductase inhibitor e.g. Fluvastatin or Atorvastatin or salts thereof) contained in a dosage form is "bioavailable", if when administered in a dosage form is released from the dosage form, absorbed and reaches, at least the same, concentration levels in plasma as any of the marketed products containing the same quantity of the same active ingredient and intended for the same use.

Although the pharmaceutical composition may be in various forms, the preferred solid forms are tablets, capsules and caplets.

As already mentioned certain HMG-CoA reductase inhibitors are susceptible to degradation/oxidation and their tendency gets stronger when they are formulated and mixed with excipients or other active substances.

Moreover, certain HMG-CoA reductase inhibitors such as Fluvastatin or Atorvastatin or salts thereof, have a relative low bulk density, poor flow properties and stick to metal surfaces during tableting. It is, therefore, necessary to employ at least a lubricant in the tablet formulation of said compositions, in order to reduce the friction during tablet compression. The lubricant deforms easily when sheared between two surfaces and, hence, when interposed between the tablet and the die wall, provides a readily deformable film that eliminates the friction between the compressed tablet and the die, so that the tablet can be removed from the die without damage.

One of the main disadvantages of the HMG-CoA reductase inhibitors is the fact that, they are very labile to acidic pH environment, and consequently many limitations concerning the choice of excipients are raised.

Moreover, all the excipients should be very carefully selected because some of them are very hydrophobic and affect negatively disintegration and dissolution while has been shown to cause bioavailability problems. The manufacturing process should also be very carefully determined because relatively high concentrations of lubricant and/or glidant reduce crashing strength and increase disintegration time especially when associated with prolonged mixing times. Furthermore, it is already known either to include alternative excipients as lubricants with or without stabilizing agents, or to use more complicated formulations and/or manufacturing processes.

It has been surprisingly found that the object of the present invention is achieved by employing a linear sulphated polysaccharide such as Carrageenan as a stabilizer.

In fact, when Carrageenan is incorporated in a pharmaceutical composition according to the present invention, it is not necessary to employ an additional buffering or alkaline agent in order to avoid the degradation of statins.

Carrageenan is a linear sulphated polysaccharide with a high molecular weight, bearing free hydroxyl and sulphate groups. The Carrageenan family has three main branches named kappa, iota and lambda which are well differentiated in terms of their properties.

The interaction between Carrageenan and the HMG-CoA reductase inhibitor contributes to the stabilization of the active ingredient by the intermolecular hydrogen bonding between the interactants. In this system Carrageenan and the active ingredient are in contact in a molecular basis. Said system protects the active ingredient from oxidation and/or elimination and/or isomerization. Thus, Carrageenan serves as a protective barrier, isolating the active ingredient against humidity and/or air oxygen and/or a low pH environment.

In that respect, the stability of fluvastatin sodium can be increased by far in solid state even in the presence of moisture. In addition to that, by releasing it in a more controlled fashion in aqueous medium, the concentration of fluvastatin sodium as a free salt will be reduced, thus giving less time for the lactonization process to occur.

This drug—polymer interaction is utilized to reduce the initial release rate of Fluvastatin and to obtain more linear release profile (zero order). The drug—polymer interaction product can form subsequently a solid dosage form such as a tablet. In particular, an interaction between X- and/or iota-carrageenan and fluvastatin is used to prepare tablets providing a constant drug release (near zero order).

Further, it has been surprisingly found that when the HMG-CoA reductase inhibitor interacts with Carrageenan and the formed interactions is then formulated in tablet, the interaction obtained is the release-controlling factor.

It has been also found that the interaction of the drug with the Carrageenan stabilise the prone to degradation "statin". The active substance is also protected from the acidic environment in the stomach, as Carrageenan competitively binds the gastric HCl and is being partially hydrolysed. It has been further found that the suggested system releases the drug in such a rate that the bioavailability of the drug is ensured.

It has been confirmed through several tests such as FT-IR spectra analysis, DSC thermal analysis, X-RD analysis, and viscosity measurements method that according to the formulation of the present invention there is chemical interaction between the Fluvastatin sodium and Carrageenan.

Figure 4:
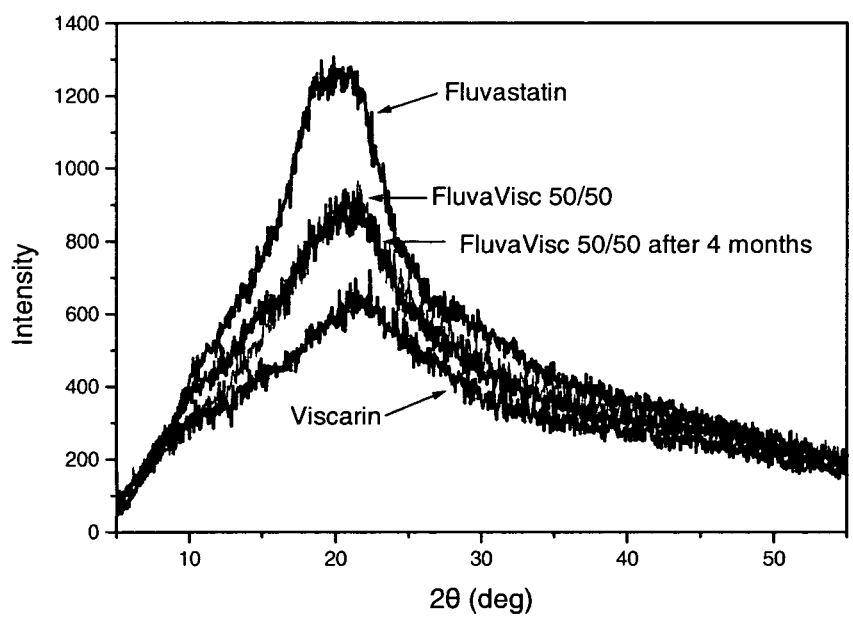
FIGS. 4, 5 and 6 show X-RD spectrum of an amorphous Fluvastatin, Carrageenan and a mixture of Fluvastatin and Carrageenan according to the present invention directly after preparation and after 4 months storage in conditions of an accelerated ageing.
Figure 5:
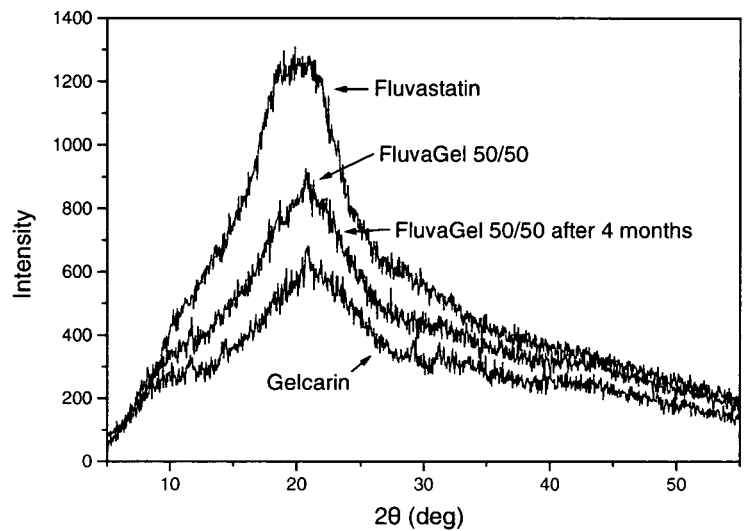
Figure 6:
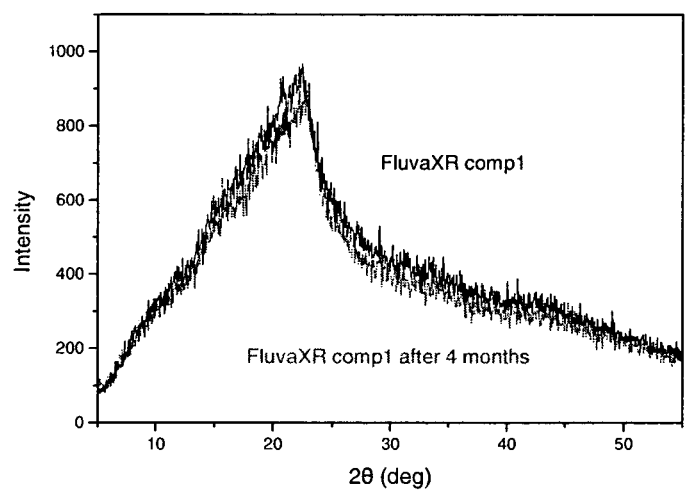

In addition, as shown in FIGS. 4 to 6 by the X-RD analysis, Fluvastatin is completely amorphous since only a broad peak is recorded with a maximum at around $2\theta=20$ deg, and i-carrageenan (Gelcarin) is also amorphous with a broad peak at $2\theta=21.50$ deg. The mixture of an amorphous statin and Carrageenan does not promote the crystallization of said Statin (Fluvastatin remains amorphous), as it has been confirmed by X-RD analysis wherein all the recorded characteristic broad peaks were unchanged after 4 months storage in accelerated conditions (40° C. and 75% RH). The maximum of the peak is now placed between the two initial peaks of Fluvastatin and i-carrageenan at $2\theta=20.90$ deg. This indicates that the crystal of the active ingredient remained invariable after mixed with Carrageenan. The crystal properties remain also unchanged after four months in the same conditions when the mixture is incorporated in a pharmaceutical composition with other excipients. The stabilization could be the result of hydrogen bonding between the statin hydroxylic groups and Carrageenan. No peaks corresponding to any crystalline form of Fluvastatin are observed before or after storage indicating that the mixture is stabilized.

Further, λ-carrageenan (under the trademark Viscarin) is partially crystalline, showing low intensity peaks at $2\theta=11.75, 14.40, 20.80, 29.20$ and $31.30$ deg. Most of these peaks do not appear when λ-carrageenan is blended with fluvastatin in (1/1) ratio and only a small peak at $2\theta=20.80$ deg is observed indicating that the mixture is stabilized and remains amorphous. The mixture is also amorphous after 4 months at 40° C./75% RH.

The addition of other optional excipients does not affect the crystallity of fluvastatin or i- and λ-carrageenan, as depicted from the XRD analysis of the finished formulation after 4 months at 40° C./75% RH.

Further, a Differential Scanning Calorimetry (DSC) analysis has been performed, wherein i-carrageenan shows a sharp decomposition peak (exothermic) in DSC thermogram at 188° C. whereas λ-carrageenan at 210° C. In the thermograms of the mixtures with low fluvastatin concentration this peak is broader, whilst in relatively high fluvastatin concentration it appears at higher temperatures. In fact, the endothermic peak appears 40-50 degrees higher demonstrating thus, that the stabilization of the mixture is due to strong hydrogen bonding interactions between the interactants. In fact, the interaction between fluvastatin sodium and the carrageenan polymer is formed by the intermolecular hydrogen bonding among fluvastatin sodium and carrageenan.

Figure 7:
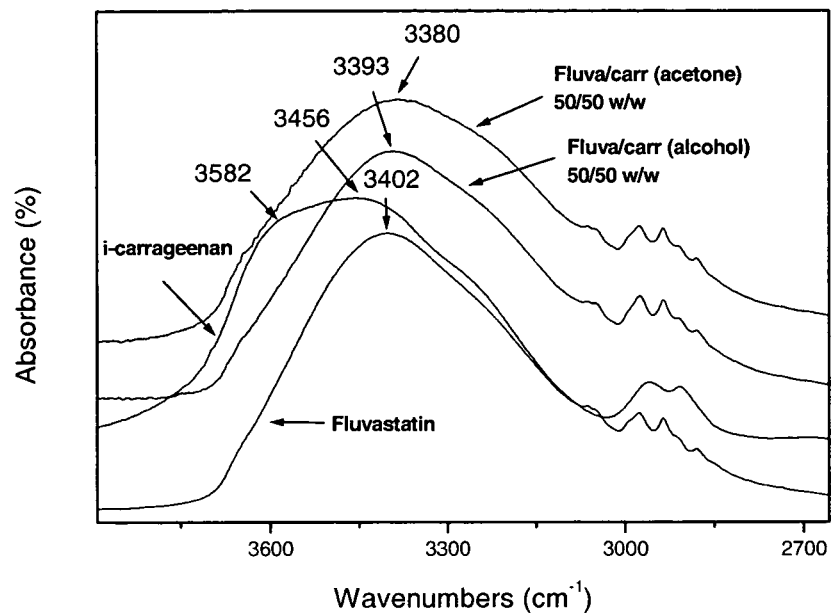
FIGS. 7 and 8 show a FT-IR spectrum of Fluvastatin, Carrageenan and a mixture of both according to the present invention.
Figure 8:
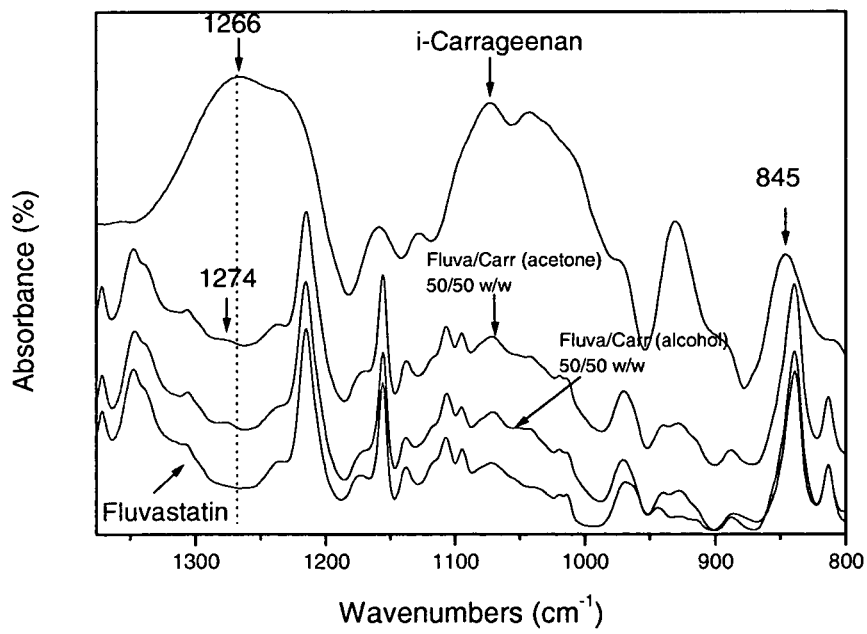

Moreover, as shown in FIGS. 7 and 8, a FT-IR spectra analysis shows remarkable shifts of characteristic absorption peaks of the two substances corresponding to their hydroxylic groups. In specific, the hydroxy groups of fluvastatin absorb at 3402 $cm^{-1}$ and said of i-carrageenan at 3456 and a shoulder at 3582 $cm^{-1}$. In the case of mixtures prepared by a water-free process using acetone or ethanol as solvents, these peaks are shifted to 3380 και 3393 $cm^{-1}$ and due to hydrogen bonds between the hydroxylic groups of fluvastatin and the —$SO_2$ groups of i-carrageenan. The peak corresponding to —$SO_2$ groups of i-carrageenan is shifted from 1266 to 1274 $cm^{-1}$. These results provide evidence for the statin-carrageenan interaction. In addition, similar results have been provided for the statin-λ-carrageenan interaction.

Further, a test for the viscosity has been performed according to Ostwald's technique with a borosilicate glass type "Techniko bs/u". Specifically, the interactions provided a significant increase of their aqueous solutions viscosity.

The concentration of the aqueous solutions was 0.1% w/v and the temperature 20° C. for all the trials.

Aqueous solutions of fluvastatin sodium (API), λ-Carrageenan, iota-Carrageenan, mixture Fluvastatin/λ-Carrageenan in 1/1 ratio and fluvastatin/iota-Carrageenan in 1/1 ratio (solid dispersions with EtOH) were tested.

The results, presented in Table 1, show a significant increase regarding the viscosity of the mixtures providing additional evidence of the statin-carrageenan interaction.

TABLE 1

VISCOSITY OF AQUEOUS SOLUTIONS OF FLUVASTATIN, ι-CARRAGEENAN, λ-CARRAGEENAN AND MIXTURES THEREOF
Concentration: 0.1% w/v
Temperature: 20° C.

| SAMPLE | viscosity(cp) |
|---|---|
| Water (reference standard) | 1.00 |
| Fluvastatin Sodium (API) | 1.15 |
| Viscarin GP-209NF | 2.00 |
| Gelcarin GP-379NF | 1.69 |
| Mixture Fluvastatin/Viscarin 1/1 (solid dispersion) | 8.15 |
| Mixture Fluvastatin/Gelcarin 1/1 (solid dispersion) | 3.62 |

A mixture of the active ingredient (HMG CoA reductase inhibitor, especially Fluvastatin or Atorvastatin or salts thereof) with a suitable amount of a sulphated polysaccharides is formed, and subsequently kneading the blend with a suitable water-free solvent e.g. an appropriate amount of ethanol and/or acetone and drying the wetted mass. After sieving the dried mass, any optional additional excipient is then added. The composition is then mixed until uniform. The resulting composition may then be compressed.

Moreover, any excipient may optionally be added to the above composition, provided that they are compatible with the active ingredient of the composition, in order to overcome problems associated with the poor flow properties and unfavorable pharmacotechnical characteristics of these substances, and in order to increase the stability of the drug and the self-life of the pharmaceutical product, and provide a product exhibiting excellent bioavailability.

The present invention can be applied in the formulation of tablets, capsules, caplets, sachets or other solid dosage forms of an active ingredient having stability problems.

Another essential advantage of the present invention is that the solid dosage form according to the present invention ensures excellent bioavailability of the active ingredient. Furthermore, it is possible to prepare dosage forms of different strength using appropriate quantity of the same composition, thereby limiting the cost of production and minimizing the number, and consequently the cost, of clinical studies required for the approval of the product by the authorities.

A further advantage of the present invention is that upon administration of the composition to a patient, the high levels of carrageenan facilitate the sustained solubilization of the active ingredient.

The manufacturing process for preparation according to the present invention is simpler and inexpensive in comparison to any other conventional method.

Therefore, in a first embodiment, the present invention provides a pharmaceutical composition comprising from about 0.5% to 60% by weight of Fluvastatin or the salt thereof and from about 0.1% to 60% by weight of Carrageenan. The weight ratio of the Fluvastatin to Carrageenan is preferably 1:5 to 2:1.

Preferred pharmaceutical compositions according to the present invention comprise approximately 0.5% to 50% and more preferably 0.75% to 35% by weight of Fluvastatin or the salt thereof.

More preferred pharmaceutical compositions according to the present invention comprise approximately 0.1% to 60% by weight of Carrageenan.

The preferred pharmaceutical compositions are in the form of solid dosage forms such as tablets, capsules, caplets, troches, pastilles, pills, lozenges and the like, in all shapes and sizes, coated or uncoated.

All percentages stated herein are weight percentages based on total composition weight, unless otherwise stated.

Another embodiment of the present invention is the use of the direct compression process for the preparation of solid dosage forms such as tablets containing Fluvastatin or Atorvastatin or salts thereof, which is one of the most economical methods.

The direct compression process of the present invention for the preparation of solid dosage forms such as tablets containing Fluvastatin or Atorvastatin or salts thereof as an active ingredient comprises:

Forming a homogenous mixture by mixing the total quantity of the active ingredient with the total quantity of a suitable amount of Carrageenan or mixtures thereof as a stabilizer;

Sieving the above mixture on a sieve, and subsequently;

Adding to the sieved mixture the total quantities of at least one optionally excipient such as a binder, a diluent, a disintegrant, a lubricant and/or a glidant and mixing until uniform, and Formulating the resulting mixture in a solid dosage form by compressing it into a desired tablet form with a force more than 400 kp.

The final mixture of the composition can be compressed into tablets or caplets, filled into capsules, or processed into another solid form.

The pharmaceutical compositions according to the present invention are characterized by excellent pharmacotechnical properties, such as homogeneity, flowability and compressibility. Thanks to these properties, the solid dosage forms prepared by the above process exhibit excellent technical characteristics including disintegration time, dissolution rate, hardness, resistance to crashing, friability and stability, as better illustrated by the following measurements during the stage of the development of the products.

One of the most critical pharmacotechnical tests, is the Dissolution test as it is strongly correlated with the bioavailability of the product. For the dissolution method a Paddle Apparatus was used 50 rpm, 37° C., time 30 min, while as a dissolution medium 900 ml of $H_2O$ was used.

| Dissolution profiles | | | | |
|---|---|---|---|---|
| hours | Comp 1 | Comp 2 | Comp 3 | Comp 4 |
| 1 | 2.37 | 1.85 | 2.59 | 2.75 |
| 2 | 6.20 | 4.20 | 6.62 | 6.49 |
| 4 | 15.98 | 15.09 | 17.59 | 18.92 |
| 6 | 27.63 | 26.05 | 30.79 | 33.21 |
| 8 | 39.23 | 39.72 | 43.35 | 49.39 |
| 10 | 51.13 | 55.33 | 54.81 | 63.06 |
| 12 | 60.52 | 67.65 | 64.46 | 73.22 |
| 14 | 68.84 | 79.90 | 71.09 | 80.99 |
| 16 | 76.85 | 90.55 | 80.31 | 87.06 |
| 18 | 84.76 | 93.05 | 86.62 | 92.04 |

The most preferable compositions described below were investigated for their scalability, while a process validation was performed in order to prove the repeatability and accuracy of the manufacturing process and the proposed formulations.

The validation process showed that the compositions and the manufacturing process are suitable in order to provide a repeatable and high quality product.

One of the main objects of the present invention was to prepare a product with acceptable stability. For this reason 3 batches of each composition were exposed to normal and accelerated stability studies according to the current ICH guidelines.

The following compositions were used.

| | Compositions | | | |
|---|---|---|---|---|
| Ingredients | Comp 1 mg per tab | Comp 2 mg per tab | Comp 3 mg per tab | Comp 4 mg per tab |
| Internal Phase | 80 | 80 | 80 | 80 |
| Fluvastatin Sodium | 84.2 | 84.2 | 84.2 | 84.2 |
| Viscarin | 91.6 | 98.0 | 90.1 | 85.0 |
| Gelcarin GP-379NF | 91.6 | 98.0 | 90.1 | 85.0 |
| MCC | 29.6 | 36.0 | 28.1 | 112.0 |
| Mg Stearate | 1.0 | 1.8 | 3.4 | 1.0 |

-continued

| | Compositions | | | |
|---|---|---|---|---|
| Ingredients | Comp 1 mg per tab | Comp 2 mg per tab | Comp 3 mg per tab | Comp 4 mg per tab |
| External Phase | | | | |
| Mg Stearate | 2.0 | 2.0 | 1.1 | 2.8 |
| Aerosil | | | 3.0 | |
| Total | 300.0 | 320.0 | 300.0 | 370.0 |

The tablets were packed in into containers impervious to water vapor e.g. PVC/PVDC and stored in appropriate stability chambers at a temperature of 25° C.±2° C. and relative humidity of 60%±5% for normal conditions and at a temperature of 40° C. and relative humidity of 75% for accelerated conditions. The tablets were tested in predetermined time intervals.

The frequency of the testing, the specific tests and results indicated for composition 1 are described in the stability table (TABLE 2).

The results show a good stability of the product and compatibility between the drug substance and the excipients proposed by the present invention. The excellent results regarding the physicochemical characteristics, the excellent stability of the product as well as the simple and economic manufacturing process indicate the advantages of the present invention relative to the commonly used methods and excipients for the formulation of Fluvaststin or Atorvastatin.

The pharmaceutical compositions of the present invention may also contain one or more additional formulation ingredients selected from a wide variety of excipients. According to the desired properties of the composition, any number of ingredients may be selected, alone or in combination, based upon their known uses in preparation of solid dosage form compositions (tablet compositions).

Such ingredients include, but are not limited to, diluents, binders, compression aids, disintegrants, glidants, lubricants, flavors, water scavengers, colorants, sweetener, coating agents and preservatives.

The optional excipients must be compatible with the HMG-CoA reductase inhibitor so that it does not interfere with it in the composition.

Diluents may be, for example, calcium carbonate, calcium phosphate dibasic, calcium phosphate tribasic, calcium sulfate, microcrystalline cellulose, microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, maltose maltodextrin, maltitol.

TABLE 2

STABILITY AT 40° C. ± 2° C. TEMPERATURE AND 75 ± 5% RELATIVE HUMIDITY
Fluvastatin 80 mg

| | | Time In Months | |
|---|---|---|---|
| Control | Specification | 0 | 3 |
| Appearance | Light yellow round biconvex tablets 10.1 ± 0.1 mm in diameter and 3.6 mm ± 0.2 mm in thickness | No change | No change |

TABLE 2-continued

STABILITY AT 40° C. ± 2° C. TEMPERATURE AND 75 ± 5% RELATIVE HUMIDITY
Fluvastatin 80 mg

| Control | Specification | Time In Months 0 | 3 |
|---|---|---|---|
| Assay (by HPLC) | 95.0-105.0% | 100.6% | 99.2% |
| Dissolution (Paddles, 1000 ml water, 50 rpm) | Apparatus paddles, 50 rpm | | |
| | each tablet <15% in 1 h | 5.7% in 1 h | 6.0% in 1 h |
| | each tablet 35-55% in 4 h | 45.0% in 4 h | 50.6% in 4 h |
| | each tablet >80% in 12 h | 98.4% in 12 h | 88.2% in 12 h |
| Related substances | | | |
| Fluvastatin anti-isomer | NMT 0.80% | 0.10% | 0.11% |
| 3-hydroxy-5-keto fluvastatin (at 365 nm) | NMT 0.50% | 0.01% | 0.02% |
| Fluvastatin t-butyl ester | NMT 0.20% | ND | ND |
| Fluvastatin Hydroxy-diene | NMT 0.10% | 0.04% | 0.04% |
| Single unknown | NMT 0.50% | Unknown RRT 1.41: 0.02% Unknown RRT 1.87: 0.05% | Unknown RRT 1.41: 0.02% Unknown RRT 1.87: 0.07% |
| TOTAL | NMT 1.8% | 0.22% | 0.26% |

Binders may be, for example, acacia mucilage, alginic acid, carbomer, carboxymethylcellulose calcium, carboxymethylcellulose sodium, microcrystalline cellulose, powdered cellulose, ethyl cellulose, gelatin, liquid glucose, guar gum, hydroxyethyl cellulose, hydroxypropyl cellulose, hydroxypropylmethyl cellulose, maltodextrin, methylcellulose, polydextrose, polyethylene oxide, povidone, sodium alginate, starch paste, pregelatinized starch, sucrose. Disintegrants may be, for example, alginic acid, carbon dioxide, carboxymethylcellulose calcium, carboxymethylcellulose sodium, microcrystalline cellulose, powdered cellulose, croscarmelose sodium, crospovidone, sodium docusate, guar gum, hydroxypropyl cellulose, methylcellulose, polacrilin potassium, poloxamer, povidone, sodium alginate, sodium glycine carbonate, sodium laulyl sulfate, sodium starch glycolate, starch, pregelatinized starch. Glidants may be, for example, calcium silicate, powdered cellulose, starch, talc.

Lubricants e.g. Mg state, aerosil, polyethylene glycol 4000, polyethylene glycol 6000, sodium lauryl sulfate, starch, talc.

Still another embodiment of the present invention is the use of Carrageenan as an agent to improve flow properties of HMG-CoA reductase inhibitor/Fluvastatin/Atorvastatin and/or to prevent sticking to parts of the processing machines, for example tableting machine and/or to protect and stabilize hydrolysis and/or oxidation susceptible pharmaceutical substances.

The following examples illustrate preferred embodiments in accordance with the present invention without limiting the scope or spirit of the invention:

EXAMPLES

Example 1:
Tablet of 80 mg Fluvastatin (Comp. 1)

| 80 mg tablets Ingredients | % of total weight | Mg per tab |
|---|---|---|
| Fluvastatin Sodium | 28.07 | 84.2 |
| Viscarin GP-209NF | 30.53 | 91.6 |
| Gelcarin GP-379NF | 30.53 | 91.6 |
| McC | 9.87 | 29.6 |
| Mg Stearate | 1.00 | 3.0 |
| Total | 100.00 | 300.0 |

Tablets of the above formulation were prepared according to the following manufacturing process: Viscarin and Gelcarin were admixed and subsequently wet granulated using a water—free solvent specifically an ethanolic solution (absolute ethanol) of Fluvastatin Sodium. The wetted mass was then dried, passed through a sieve to achieve the desired granule size and further mixed with McC and Magnesium stearate.

The final blend was then compressed directly into tablets in a tableting machine with round punches of a 10mm diameter. The tablets were packed into blisters of PVC-PVDC.

The bulk mixture showed satisfactory flow and could also be filled into capsules or sachets or compressed into tablets. The later solution was selected and the produced tablets were tested for hardness, friability, disintegration, and water content. All tests were performed according to European Pharmacopoeia 5.1 and were well within the specifications. Dissolution test in 900 ml water, 50 rpm Paddle Apparatus has been performed (see FIG. 1).

Tablets of the same formulation of example 1 were also prepared using the procedure of Example 1 with the exception that acetone was used as a water-free solvent.

Tablets were produced and tested for content uniformity, disintegration, water content and dissolution proving that they are meeting the specifications.

Example 2:
Tablet of 80 mg Fluvastatin (Comp. 2)

| 80 mg tabs Ingredients | % | mg per tab |
|---|---|---|
| Fluvastatin Sodium | 28.07 | 84.2 |
| Viscarin GP-209NF | 30.53 | 98.0 |
| Gelcarin GP-379NF | 30.53 | 98.0 |
| MCC | 9.87 | 36.0 |
| Mg Stearate | 1.00 | 3.8 |
| Total | 100.00 | 320.0 |

Tablets of this formulation were prepared using the procedure of Example 1. From the produced bulk mixture, tablets weighting 300 mg were produced and tested for hardness, friability, disintegration, and water content and results were well within the specifications. Furthermore dissolution in 900 ml water, 50 rpm Paddle Apparatus has been perfomed (see FIG. 1).

Example 3

Tablets of the formulation of example 1 were prepared according to the following manufacturing process: Viscarin, Gelcarin and Fluvastatin Sodium were admixed and subsequently wet granulated using a water-free solvent specifically an absolute ethanol/acetone solution in weight ratio 1/1. The wet mass was then dried, passed through a sieve to achieve the desired granule size and further mixed with McC and Magnesium stearate, and the final blend then compressed to form tablets.

The behaviour of a specific active ingredient when combined with a retarding excipient cannot be predicted, since interactions between the retarding material on the one hand and the active ingredient and the other excipients on the other can affect the sustained action in various ways.

It is obvious form the dissolution graphs of FIG. 1, that no initial burst is observed and moreover the release follow zero order kinetics with an $R^2$=0.9889. Although carrageenan is a hydrophilic polymer and Fluvastatin is a highly soluble drug, the drug release doesn't show an initial burst and a rate depending on the square root of time (~$t^2$). This is due to the drug-carrageenan interaction. If the release was controlled by the matrix then it should be in accordance to one of the well-established release models, that is Higuchi model, Bamba model or Peppas equation. According to Higuchi law which applies for hydrophilic matrices wherein the release controlling factor is the swelling of the matrix and the diffusion of the drug through the gellified polymer.

$$\frac{Mt}{M\infty} = k_H \sqrt{t} + a$$

Where: Mt: drug release in time t, $M_0$: initial drug concentration in the matrix, $k_H$: release rate, a: constant The formulation of the present invention does not correspond to this model because the release is not proportional to the square root of time.

According to Bamba law which is applicable for water soluble drugs released by diffusion motivate by water penetration in the matrix:

$$\frac{Mt}{M\infty} = e^a \cdot e^{kt}$$

Where: Mt: the amount of drug released at time t, $M_0$: initial drug concentration in the matrix, k: release rate, a: constant.

The formulation of present invention does not obey the Bamba law either.

According to Peppas law which applies in hydrophilic matrices wherein the release controlling mechanism is swelling—diffusion and macromolecular relaxation of the matrix there are three phases: during phase 1 swelling and macromolecular relaxation of the matrix takes place and the drug release is less than <5%, during phase 2 the drug is released by diffusion and macromolecular relaxation is carried on until the drug is release up to 75%. The equation that mathematically describes the phenomenon is $M_t/M_{oo}=k*t^n$. Finally, during phase 3 swelling—diffusion is taking place to complete release of the drug.

According to Peppas later theory the two main mechanisms for the drug release from hydrophilic matrices are the diffusion and the macromolecular relaxation.

The diffusion corresponds to normal Fickian diffusion (n=0.45 for cylinder) and the macromolecular relaxation corresponds to Case II transportation (n=0.89 for cylinder) as shown in the following table:

| exponent n level | Cylinder | Sphere | Kinetic |
|---|---|---|---|
| 0.5 | 0.45 | 0.43 | Normal diffusion-FICK law |
| 0.5 < n < 1 | 0.45 < n < 0.89 | 0.43 < n < 0.85 | Anomalous |
| 1 | 0.89 | 0.85 | Case II transportation |
| n > 1 | n > 0.89 | n > 0.85 | Super-Case II transportation |

The formulation of present invention does not correspond to phase 2 of the Peppas law. Specifically, n>1 (present invention n=1.16) for drug release 5-75% and n=1.17 for the overall release.

The fact that the formulation of the present invention does not corresponds to any of the known models further proves that the release is caused and controlled by the interaction between active ingredient and carrageneen and specifically the removal of the drug from the complex.

Moreover, the kneading with water-free solvent, or solution containing the active, is essential for the formation of the interaction. However, it was surprisingly found that tablets produced by simple mixing showed similar dissolution profile with the formulation produced by kneading, provided that the tablets were compressed under such pressure that results in tablets with hardness of more than 40 Nt.

Examples 4 and 5 illustrate the above finding. It was found that the applied force capable to produce tablets with the desired hardness is more than 400 kp in rotary tableting machine.

Example 4

Tablets of the formulation of example 1 were prepared according to the following manufacturing process: Viscarin, Gelcarin, Fluvastatin Sodium and all the other excipients were admixed together and subsequently the blend was compressed with a force more than 400 kp (about 500 kp) to form tablets.

Figure 2:
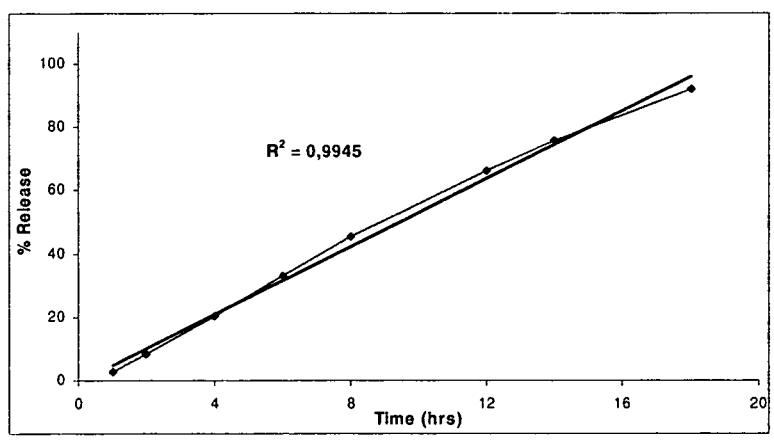
FIG. 2 shows dissolution profile of composition of example 4 according to the present invention.

The resulting tablets hardness was 45-50 Nt. The dissolution profile is given in the FIG. 2.

Example 5

Figure 3:
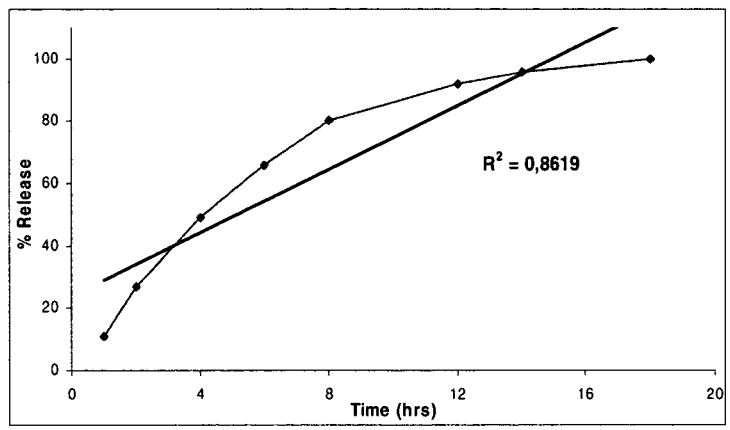
FIG. 3 shows dissolution profile of composition of example 5.

Tablets according to the formulation of example 1 were also prepared by mixing the ingredients all together. The blend was compressed 10 mm diameter tablets with less than 400 kp force (about 300 kp) and the resulting tablets hardness was 30-35 Nt. The dissolution profile, given in the FIG. 3, is in accordance with the known release models and has all the drawbacks of common sustained release systems including the initial burst and non-linear drug release:

The fact that tablets of certain hardness show essential different dissolution profile from those of lower, suggests that the interaction of carrageenan-statin can be formed in-situ following the wetting of the tablets with a liquid medium that dissolves the drug and/or the polymer. The liquid medium may be water or gastric fluid. It is, thus, crucial the hardness of the tablets to be more than 45 Nt when they are produced by simple mixing and direct compression, in order to show the characteristics of the present invention.

These results demonstrate that dissolution profile remains unaffected besides the lower strength, proving that pharmacotechnical linearity i.e. proportional change in amount of excipients and active and While the present invention has been described with respect to the particular embodiments, it will be apparent to those skilled in the art that various changes and modifications may be made in the invention without departing from the spirit and scope thereof, as defined in the appended claims.

The invention claimed is:

1. A sustained release pharmaceutical composition for oral administration comprising:
   an active ingredient, wherein said active ingredient comprises Fluvastatin or a pharmaceutically acceptable salt thereof;
   a stabilizer, wherein said stabilizer comprises an effective amount of a mixture of λ-Carrageenan and ι-Carrageenan; and
   wherein the weight ratio of the active ingredient to the stabilizer is in the range of 1/5 to 2/1.

2. The pharmaceutical composition according to claim 1, wherein said active ingredient is in hydrogen bonding interaction with said stabilizer.

3. The pharmaceutical composition according to claim 2, wherein it does not comprise any buffering or alkaline agent.

4. The pharmaceutical composition according to claim 1, wherein the weight of said active ingredient is in the range of 0.75% to 35% of the total weight.

5. The pharmaceutical composition according to claim 2, wherein the weight of said stabilizer is in the range of 0.1% to 60% of the total weight.

6. The pharmaceutical composition according to claim 1, further comprising at least one optionally excipient selected from the group consisting of diluents, binders, disintegrants, lubricants, and glidants.

7. The pharmaceutical composition according to claim 1, wherein said composition is in a solid dosage form and wherein said solid dosage form comprises one of a tablet, capsule or sachet.

8. A process for the preparation of a sustained release solid dosage form for oral administration comprising:
   Providing an active ingredient, wherein said active ingredient comprises Fluvastatin or a pharmaceutically acceptable salt thereof;
   Providing a stabilizer, wherein said stabilizer comprises an effective amount of a mixture of λ-Carrageenan and ι-Carrageenan, and wherein the weight ratio of the active ingredient to the stabilizer is in the range of 1/5 to 2/1;
   Forming a homogenous mixture by mixing the total quantity of said active ingredient with the total quantity of said stabilizer;
   Kneading the above mixture with a suitable water-free solvent;
   Drying the wetted mass;
   Sieving the dried mass and adding to the sieved mixture the total quantities of at least one optional excipient wherein said excipient comprises one of a binder, a diluent, a disintegrant, a lubricant and/or a glidant, and mixing until uniform; and
   Formulating the resulting mixture in a solid dosage form either by compressing it into a desired tablet form or by filling capsules or sachets.

9. A process for the preparation of a sustained release solid dosage form for oral administration comprising:
   Providing an active ingredient, wherein said active ingredient comprises Fluvastatin or a pharmaceutically acceptable salt thereof;
   Providing a stabilizer, wherein said stabilizer comprises an effective amount of a mixture of λ-Carrageenan and ι-Carrageenan, and wherein the weight ratio of the active ingredient to the stabilizer is in the range of 1/5 to 2/1;
   Forming a homogenous mixture by mixing the total quantity of said active ingredient with the total quantity of said stabilizer;
   Sieving the above mixture through a sieve;
   Adding to the sieved mixture the total quantities of at least one optional excipient wherein said excipient comprises one of a binder, a diluent, a disintegrant, a lubricant and/or a glidant, and mixing until uniform; and
   Formulating the resulting mixture in a solid dosage form by compressing it into a desired tablet form with a force more than 400 kp.

* * * * *